(12) United States Patent
DeSilva et al.

(10) Patent No.: US 10,722,626 B2
(45) Date of Patent: Jul. 28, 2020

(54) REDUNDANT-IMPELLER ARTIFICIAL HEART

(71) Applicants: Peter DeSilva, Rancho Santa Margarita, CA (US); Steve Smith, Trabuco Canyon, CA (US)

(72) Inventors: Peter DeSilva, Rancho Santa Margarita, CA (US); Steve Smith, Trabuco Canyon, CA (US)

( * ) Notice: Subject to any disclaimer, the term of this patent is extended or adjusted under 35 U.S.C. 154(b) by 0 days.

(21) Appl. No.: 16/132,291

(22) Filed: Sep. 14, 2018

(65) Prior Publication Data

US 2019/0143017 A1 May 16, 2019

Related U.S. Application Data

(63) Continuation-in-part of application No. 15/405,183, filed on Jan. 12, 2017, now Pat. No. 10,589,010.

(51) Int. Cl.
*A61M 1/10* (2006.01)
*A61M 1/12* (2006.01)

(52) U.S. Cl.
CPC ........ *A61M 1/1012* (2014.02); *A61M 1/1008* (2014.02); *A61M 1/1013* (2014.02); *A61M 1/1036* (2014.02); *A61M 1/122* (2014.02); *A61M 1/10* (2013.01); *A61M 1/1029* (2014.02); *A61M 1/1031* (2014.02); *A61M 1/1055* (2014.02); *A61M 2205/17* (2013.01)

(58) Field of Classification Search
CPC ....................................................... A61M 1/10
See application file for complete search history.

(56) References Cited

U.S. PATENT DOCUMENTS

| | | | | |
|---|---|---|---|---|
| 6,302,661 | B1* | 10/2001 | Khanwilkar | F04D 13/0646 415/900 |
| 2002/0141889 | A1* | 10/2002 | Toye | A61H 33/6063 417/366 |
| 2013/0331934 | A1* | 12/2013 | Kabir | A61F 2/24 623/3.11 |
| 2015/0066142 | A1* | 3/2015 | Smith | A61M 1/101 623/3.13 |

* cited by examiner

*Primary Examiner* — Jacqueline Woznicki
(74) *Attorney, Agent, or Firm* — Roy A. Ekstrand

(57) ABSTRACT

An artificial heart for use in a human recipient includes a housing within which a quartet of turbine pump segments are operative. The quartet of turbine pump segments is configured to provide a pair of redundant input and output turbine pump segment pairs each input and output pair being coupled by a curved passage providing a redundancy which, in turn, enhances the safety factor provided by the artificial heart. Each turbine pump segment includes an impeller forwarded for rotation and having a plurality of impeller blades together with a static deswirler positioned within the impeller output flow to reduce the swirling turbulence of the blood flow induced by the rotating impeller.

2 Claims, 5 Drawing Sheets

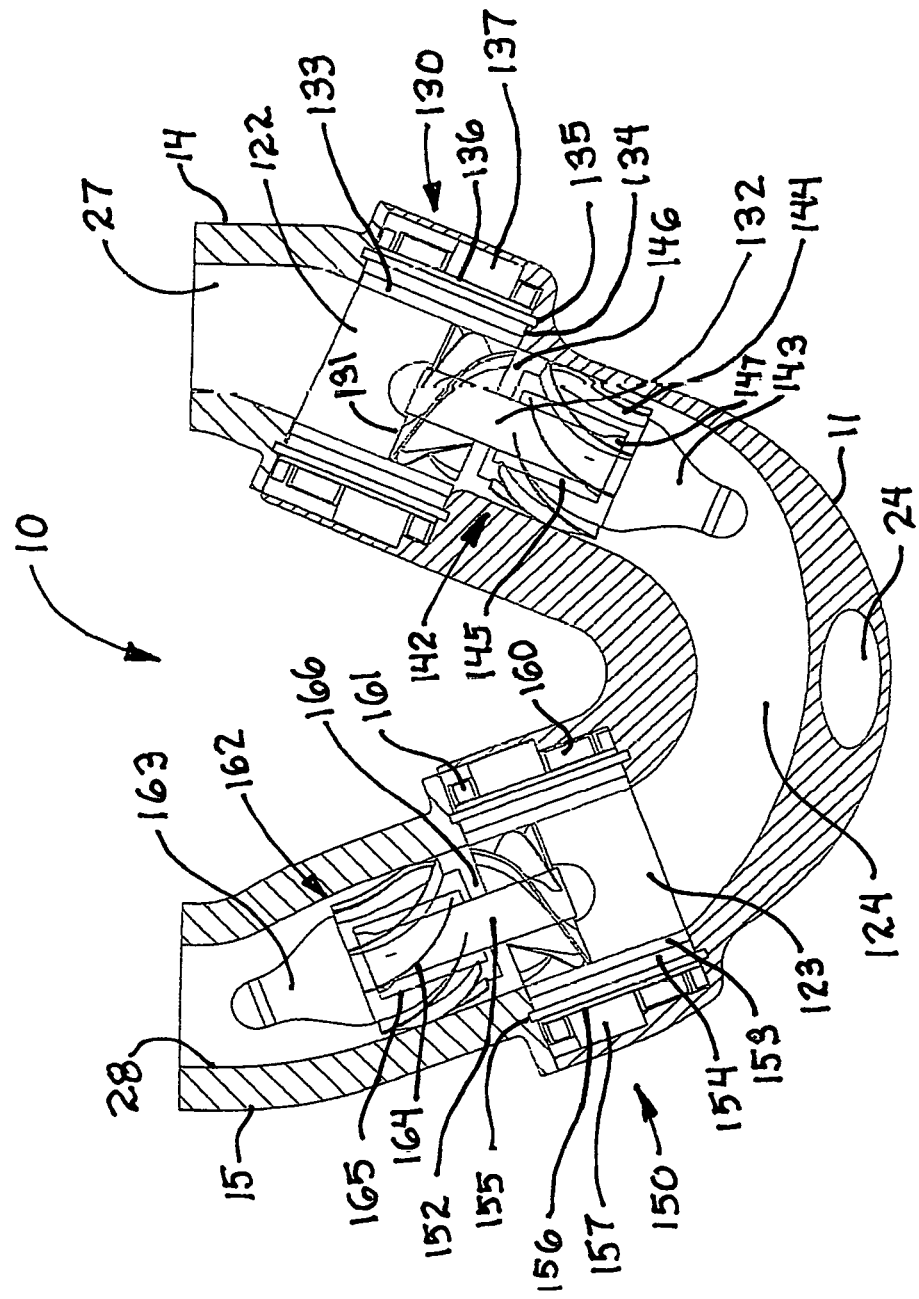

REDUNDANT-IMPELLER ARTIFICIAL HEART

CROSS-REFERENCE TO RELATED APPLICATION

This application is a Continuation-In-Part of previously filed co-pending U.S. patent application Ser. No. 15/405,183 entitled REDUNDANT-IMPELLER ARTIFICIAL HEART, filed Jan. 12, 2017 in the names of Peter DeSilva and Steve Smith, the disclosure of which is incorporated herein by reference.

FIELD OF THE INVENTION

This invention relates generally to apparatus for sustaining and continuing life for patients having failing or failed hearts and particularly to artificial heart replacement devices used therein. This invention also further relates to U.S. Pat. No. 9,314,559, issued to Steve Smith and Peter DeSilva, entitled FOUR CHAMBER REDUNDANT-IMPELLER ARTIFICIAL HEART, the disclosure of which is hereby incorporated herein by reference.

BACKGROUND OF THE INVENTION

For many years, practitioners in the medical treatment and medical device arts have endeavored to provide artificial heart devices constructed to replace a failed or failing heart within a recipient. The most basic need is the creation of a replacement pumping device which is capable of performing the basic blood pumping and circulation functions of the natural heart.

Early attempts to provide a sustainable heart replacement were severely limited by the available technologies and the state of the art at that time. Devices proved to be generally too large and unwieldy and, for the most part, impractical. With the continuing advances in the related technologies and creative arts, heart replacement devices became smaller, more reliable and, in some instances, at least partially implantable within the recipient. Such "implantable" devices have generally remained hybrid devices in that the actual pump may be implanted within the recipient while additional support apparatus remains external to the patient and remains connected to the implanted device by a plurality of connecting wires and hoses.

Because of the complexity of human body systems and the complications and consequences of heart replacement device failure, the requirements for an implantable artificial heart remain daunting. Since the long term objectives of practitioners in the medical arts include a practical implantable artificial heart that a recipient may rely upon for long periods of life independent and free of medical supervision, reliability becomes of paramount importance.

Accordingly, and by way of example, a successful artificial heart replacement device must, above all, be long lasting and reliable. The dire consequences to the device recipient brought about by device failure make this requirement all too apparent. In addition, however, the device must be small enough to be implantable within the recipient's chest and efficient enough to maintain adequate blood circulation to sustain normal life functions. The device must avoid undue stress upon the recipient's circulatory and pulmonary systems. The device must also be capable of adjusting to and compensating for different recipient activity levels and stresses.

One type of pump which has begun to show promise as a type of pumping apparatus suitable for use within an artificial human heart involves rotatable turbine type pumps. While a variety of turbine style pumps have been tried in application to artificial hearts, most utilize a rotating center shaft which supports a plurality of outwardly extending turbine blades or vanes. While turbine pumps show promise, the complex nature of human blood presents a significant number of daunting problems which, as of yet, remain largely unsolved. For example, early on in the application of turbine style pumps it became clear to practitioners that the use of conventional high-speed turbines produced unacceptable damage to blood cells. Further problems arise in that blood tends to coagulate and form like threatening clots in areas of the circulatory system or pumping apparatus in which blood is relatively static and tends collect. Still further problems arise as blood tends to form undesired clots against edges within the pumping structure. By way of further example, still more problems are created as rotating blades and vanes of turbine pumps induce corresponding turbulence and "swirling" flow patterns within the pump blood.

Accordingly, these additional requirements such as induced flow turbulence, avoidance of blood cell damage by the pumping apparatus and the prevention of the blood clot forming stagnation regions make further demands upon the heart replacement device.

In addition, because such artificial heart devices are implanted within the human recipient's chest cavity, it is essential that the size, shape and orientation of the artificial heart device the conducive to the confines of the recipient's body. Accordingly, it is an important aspect of the acceptability and practical utility of such artificial heart devices that the device minimize the intrusive potential of the device implant.

One such artificial heart device which embodies great promise, is shown in the above-referenced and incorporated U.S. Pat. No. 9,314,559 which sets forth an artificial heart for use in a human recipient that includes a housing within which a quartet of turbine pump segments are operative. The quartet of turbine pump segments provides a redundancy which in turn enhances the safety factor provided by the artificial heart. A controller is powered by a rechargeable battery and is operative to apply appropriate drive signals to the motor drives of the turbine pump segments. The battery may be implanted along with the controller to avoid the need for any external connections to the artificial heart. An inductively coupled battery charger for use outside the recipient's body is positioned proximate the battery charger to provide inductively coupled charging for use in driving the artificial heart.

A substantial number of recently explored technologies attempting to provide successful implantable artificial hearts have chosen to utilize pumping apparatus which includes a rotating impeller such as a turbine impeller or the like. While rotating turbine impeller type pumps have shown great promise for ventricular assist devices, a limitation has arisen which takes the form of rotational blood flow turbulence created by the rotating impellers of the turbine pumps. This turbulence has been found to exhibit vortex characteristics which are undesirable in application to blood pumping apparatus.

In a related art, various apparatus have been provided for reducing or mitigating the turbulence within fluid flow systems induced by the rotating pumps such as turbine pumps or the like. Such apparatus are often referred to in the art as "deswirlers" or "flow straighteners". Such devices are typically placed downstream in the fluid flow relative to the rotating pump elements with the object of counteracting the rotational turbulence component in the flow produced by the rotating pump elements. In one such element a type of "fluid collimator" is provided in which a plurality of generally small fluid passages are arranged in a parallel relationship much like a box of drinking straws. In another type of deswirler device, a plurality of vanes are situated within the fluid flow downstream of the rotating pump element.

While practitioners in the medical treatment and medical device arts have created a virtually endless number of proposed artificial heart replacement devices, there remains nonetheless a continuing unresolved need in the art for an improved, implantable, reliable and effective artificial heart replacement device which meets the stringent, unforgiving and vital requirements and challenges posed by a truly fully functioning completely implantable heart replacement device.

SUMMARY OF THE INVENTION

Accordingly, it is a general object of the present invention to provide an artificial heart replacement device which is reliable, implantable and effective. It is a more particular object of the present invention to provide an artificial heart that is sized and shaped to readily fit within the interior of a human chest cavity and abdomen. It is a more particular object of the present invention to provide an improved artificial heart replacement device which maintains a relatively turbulence free blood flow notwithstanding the use of rotating turbine pump devices.

In accordance with the present invention, there is provided an artificial heart comprising: a housing having a first input, a first output, a second input and a second output; a first turbine pump having a first deswirler operative to flow blood from the first input to the first output; a second turbine pump having a second deswirler operative to flow blood from the first input to the first output; a third turbine pump having a third deswirler operative to flow blood from the second input to the second output; and a fourth turbine pump having a fourth deswirler operative to flow blood from the second input to the second output. The artificial heart of the present invention includes an outer housing enclosure that defines a generally planar surface upon which the first and second inputs and the first and second outputs are supported. A first curved blood flow passage is coupled between the first and second turbine pumps and a second curved blood flow passage is coupled between the third and fourth turbine pump.

The present invention improves the art by providing an artificial heart comprising: a housing having a first input connector, a first output connector, a second input connector and a second output connector; a first turbine pump, having a first pump input coupled to the first input connector, and having a first pump output, the first turbine pump including a first deswirler operative to flow blood from the first input connector to the first output connector; a second turbine pump, having a second pump input, and having a second pump output coupled to the first output connector, the second turbine pump having a second deswirler operative to flow blood from the first input connector to the first output connector; a third turbine pump, having a third pump input coupled to the second input connector, and having a third pump output, the third turbine pump having a third deswirler operative to flow blood from the second input connector to the second output connector; a fourth turbine pump, having a fourth pump input, and having a fourth pump output coupled to the second output connector, the fourth turbine pump having a fourth deswirler operative to flow blood from the second input connector to the second output connector; a first curved blood flow passage coupling the first pump output to the second pump input; and a second curved blood flow passage coupling the third pump output to the fourth pump input.

In the preferred fabrication of the present invention, the use of dual pump drives and dual turbine pumps is configured to provide pump redundancy should a pump fail. In such case, the remaining operative motor/pump drives the turbine coupled thereto with sufficient capability and circulation to maintain life in the recipient until remedial intervention may be performed. In a preferred fabrication of the present invention artificial heart, the first and second turbine pumps utilize respective first and second deswirlers while the third and fourth turbine pumps utilize respective third and fourth deswirlers to provide substantially reduced turbulence blood flow. Also in the preferred fabrication of the present invention the first and second turbine pumps as well as the third and fourth turbine pumps are arranged in series pairs within the blood flow. The turbine pumps are supported within a housing defining a pair of curved blood flow passages each blood flow passage coupling the two turbine pumps in one of the series pairs of turbine pumps. In the preferred fabrication of the present invention, each of the curved blood flow passages define venturi portions.

BRIEF DESCRIPTION OF THE DRAWINGS

The features of the present invention which are believed to be novel are set forth with particularity in the appended claims. The invention, together with further objects and advantages thereof, may best be understood by reference to the following description taken in conjunction with the accompanying drawings, in the several figures of which like reference numerals identify like elements and in which:

FIG. 5 sets forth a section view of the present invention artificial heart taken along section lines 5-5 in FIG. 3.

DESCRIPTION OF THE PREFERRED EMBODIMENTS OF THE INVENTION

Figure 1:
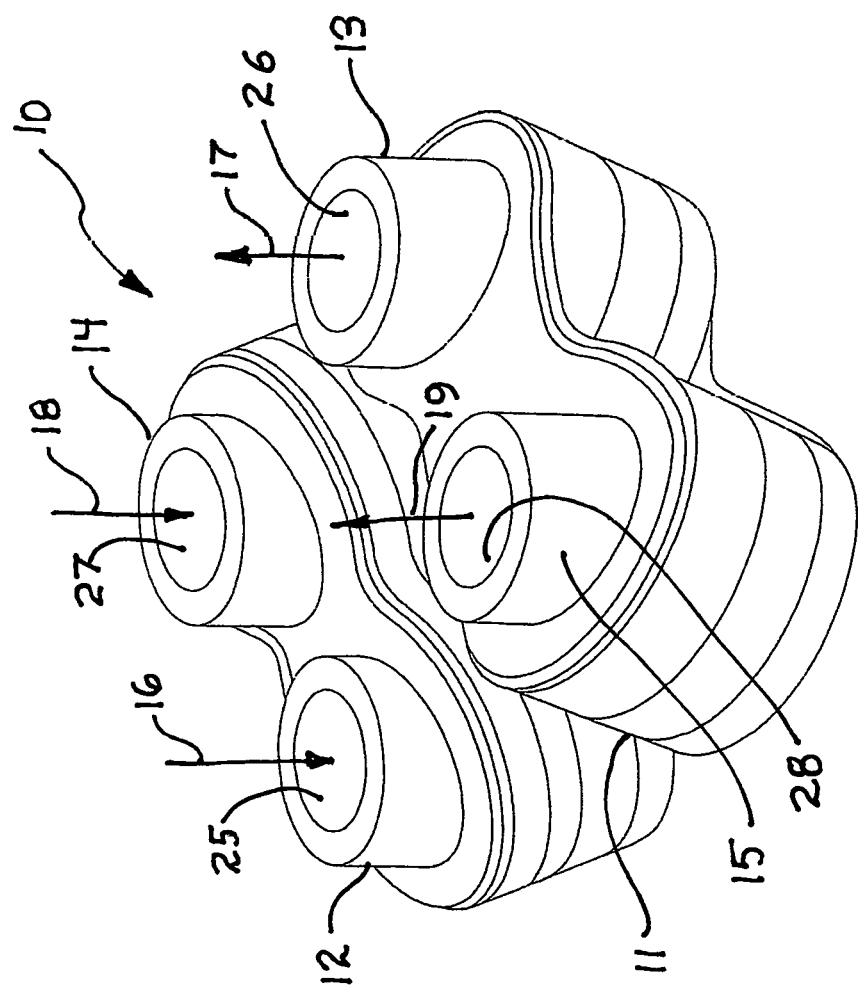
FIG. 1 sets forth a perspective view of an invention artificial heart constructed in accordance with the present invention.

FIG. 1 sets forth a perspective view of an invention artificial heart constructed in accordance with the present invention and generally referenced by numeral 10. Artificial heart 10 includes a housing 11 which supports an input coupler 12 defining an input passage 25 together with an output coupling 13 defining an output passage 26. Housing 11 further defines and input coupling 14 defining an input passage 27 and an output coupling 15 defining an output passage 28. In the anticipated utilization of the present invention artificial heart, it will be understood that artificial heart 10 is appropriately coupled to the circulatory system of a patient recipient in the manner set forth above in the above referenced incorporated patent application. It will be further understood that this coupling will utilize conventional connecting apparatus suitable for cooperation with the patient's blood vessels. Finally, it will be further understood that artificial heart 10 will be operated and controlled utilizing the power and control apparatus set forth in the above-referenced and incorporated patent application.

Accordingly, in operation blood flow from the patient's vena cava is directed into artificial heart 10 in the direction indicated by arrow 16 entering input passage 25. Thereafter, the redundant pumping apparatus set forth and described below in deuces blood flow from input 12 to emerge at output 13 in the direction indicated by arrow 17 from output passage 26. Connections then direct this flow to the pulmonary veins of the patient for circulation through the lungs after which the blood flow is redirected to artificial heart 10 at input 14 in the direction indicated by arrow 18 passing into input passage 27. Once again the redundant pumping apparatus set forth and described below in deuces blood flow from input 14 to emerge at output 15 in the direction indicated by arrow 19 passing through output passage 28 and being directed to the patient's aorta for circulation through the body. In accordance with the structure set forth below in FIGS. 4 and 5, artificial heart 10 defines a pair of blood flow coupling passages which "crisscross" within housing 11 in a manner whereby the blood flow passages pass above and below one another. To maintain blood flow volume, and reduce the overall height of housing 11 to favor implanted ability of artificial heart 10, the blood flow passages are preferably oval shaped rather than circular cross-section.

Figure 2:
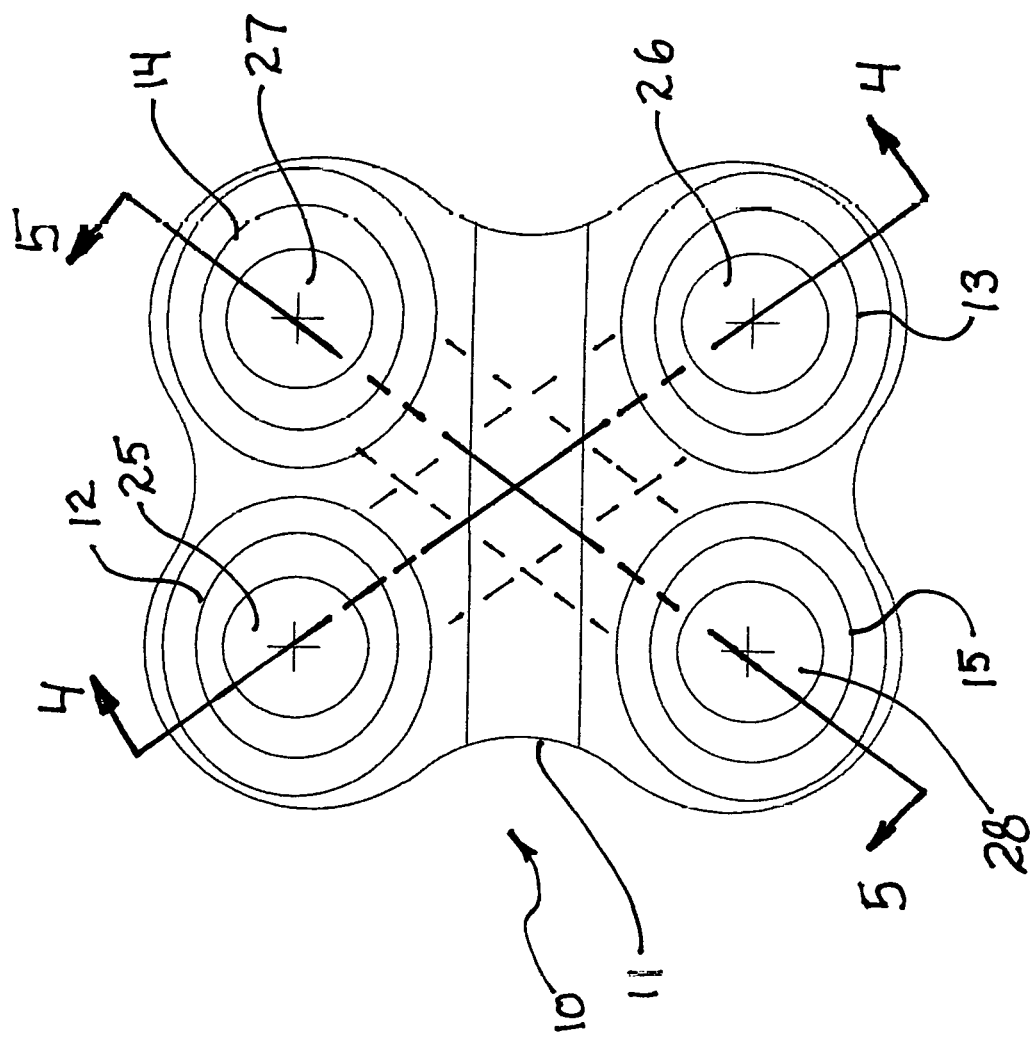
FIG. 2 sets forth a top view of the present invention artificial heart.

FIG. 2 sets forth a top view of artificial heart 10. As described above, artificial heart 10 includes a housing 11 which supports an input coupler 12 defining an input passage 25 together with an output coupling 13 defining an output passage 26. Housing 11 further defines and input coupling 14 defining an input passage 27 and an output coupling 15 defining an output passage 28.

Figure 3:
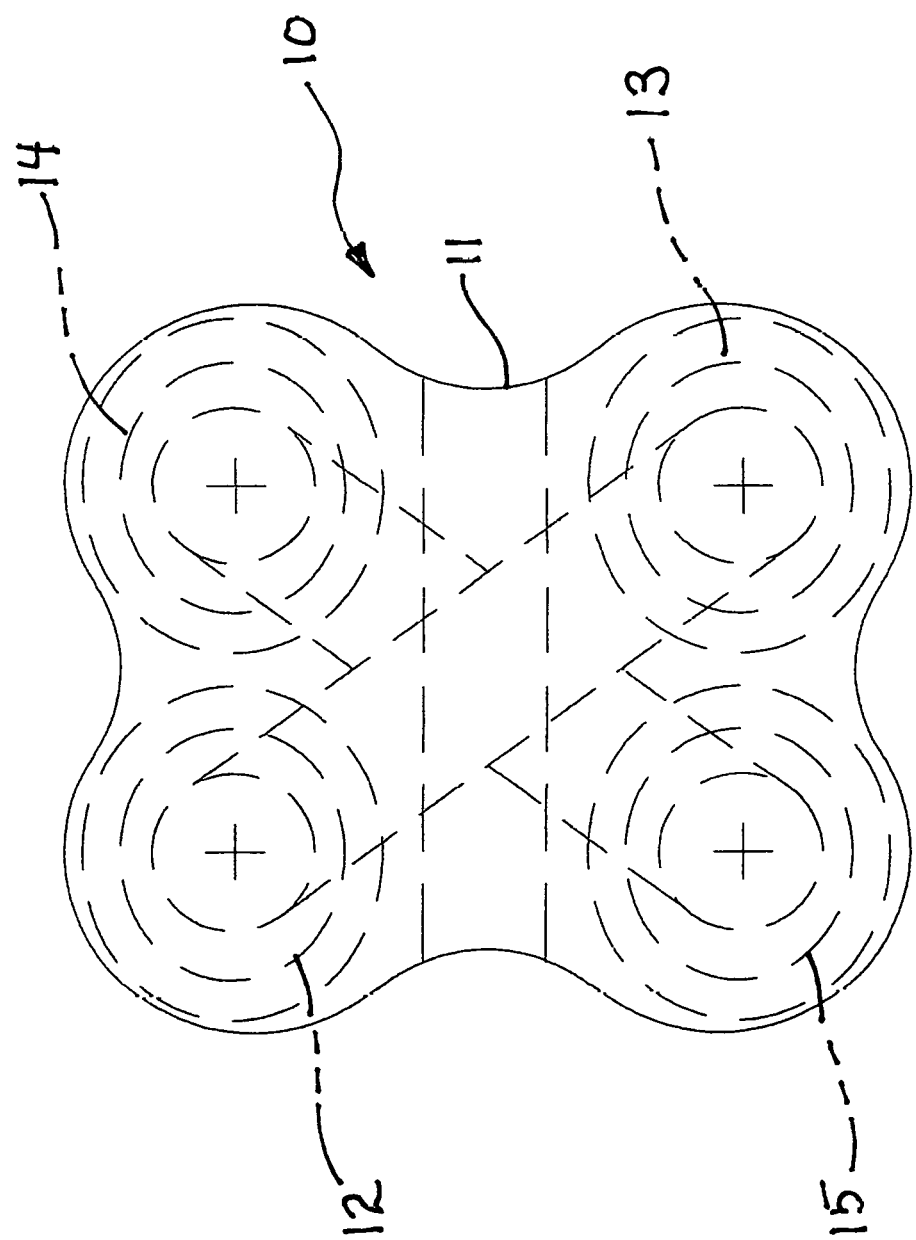
FIG. 3 sets forth a bottom view of the present invention artificial heart.

FIG. 3 sets forth a bottom view of artificial heart 10 showing the relative positions of input coupler 12, output coupler 13, input coupler 14 and output coupler 15. Also shown in FIG. 3 in dashed line representation are the above-mentioned crisscross blood flow passages.

Figure 4:
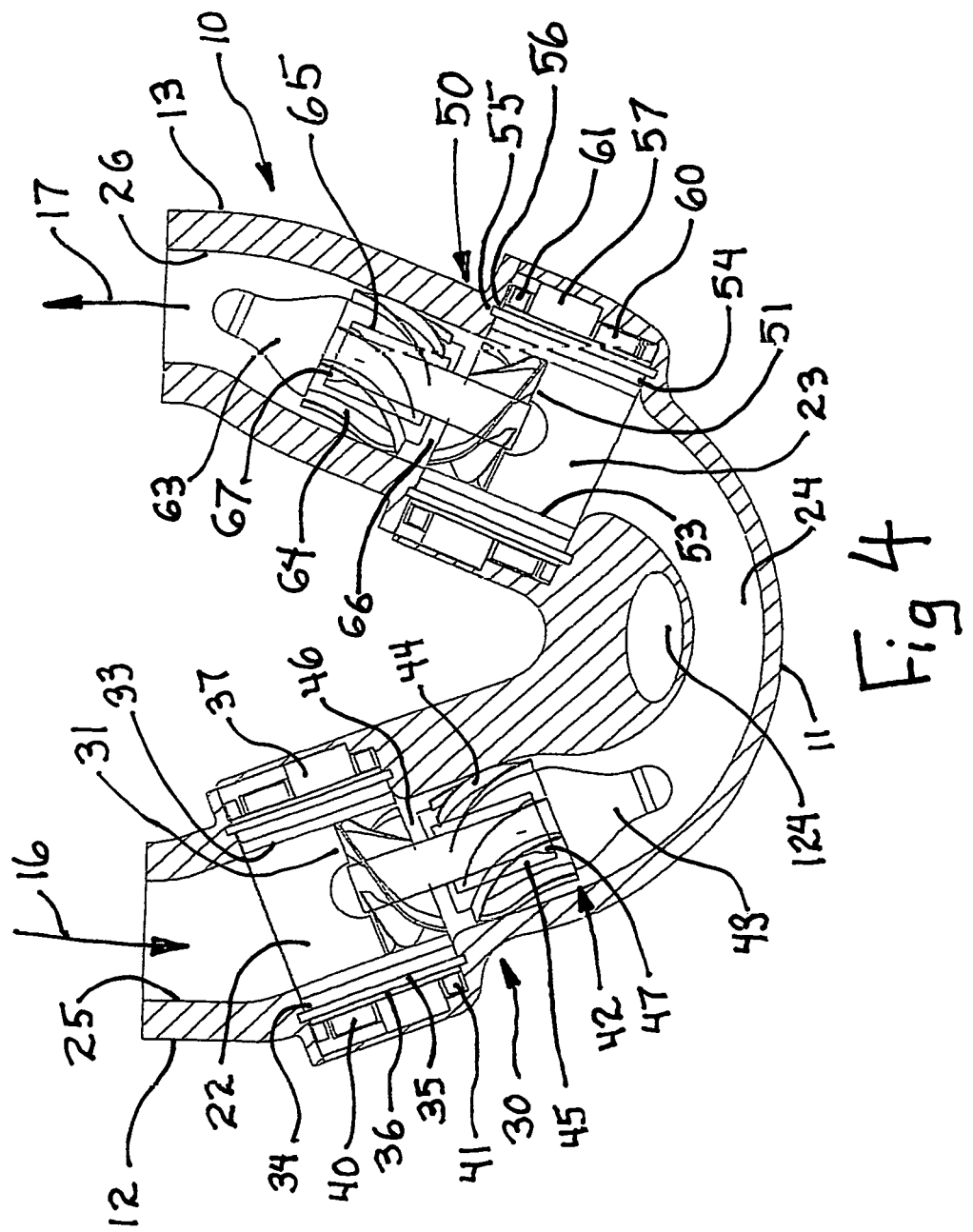
FIG. 4 sets forth a section view of the present invention artificial heart taken along section lines 4-4 in FIG. 3.

FIG. 4 sets forth a section view of artificial heart 10 taken along section lines 4-4 in FIG. 2. As described above artificial heart 10 includes a housing 11 supporting input coupler 12 and output coupler 13. Input coupler 12 further defines an input passage 25 extending through input coupler 12. Correspondingly, output coupler 13 defines an output passage 26 extending through output coupler 13. Housing 11 further defines a pump receptacle 22 within which a turbine pump 30 is supported. Housing 11 also further defines a pump receptacle 23 within which a turbine pump 50 is supported. Pump receptacles 22 and 23 are coupled by a Venturi passage 24 such that a continuous blood flow passage between input passage 25 of input coupler 12 and output passage 26 of output coupler 13 is formed. Also shown is crisscrossing Venturi passage 124. It should be noted that passage 124 and 24 are oval in cross section to reduce the overall height of artificial heart 10.

Turbine pump 30 includes a turbine impeller 31 supported upon an arbor 32. Turbine pump 30 further includes a generally cylindrical rotor 33 which is joined to the outer edges of turbine impeller 31 and is therefore rotatable therewith. A cylindrical isolator 35 is preferably formed of a suitable glass material and is fixed to the interior of pump receptacle 22 of housing 11. Isolator 35 is spaced from rotor 33 such that an air gap 34 is formed between rotor 33 and isolator 35. A motor core 36 encloses isolator 35 and is similarly fixed within pump receptacle 22. Turbine pump 30 further includes an outer core ring 37 encircling the outer surface of motor core 36. Turbine pump 30 further includes windings 40 and 41 on either side of outer core ring 37 which similarly encircle motor core 36.

Turbine pump 30 further includes a deswirler 42 having a deswirler body 43 which supports a plurality of curved deswirler vanes 44. Deswirler vanes 44 extend from deswirler body 43 and are fixed within the interior of Venturi passage 24 of housing 11 and secure the position of deswirler 42 therein. Deswirler body 43 further supports a bushing 45 which in turn receives the remaining end of arbor 32. A flared portion 47 is formed between the end of arbor 32 and the end of bushing 45 to provide a thrust load carrying surface which maintains arbor 32 within bushing 45. Arbor 32 is rotatable within bushing 45 such that a bearing is formed therebetween. In the preferred fabrication of the present invention, arbor 32 and bushing 45 are made of a jewel bearing material such as sapphire, or the like.

Turbine pump 50 is virtually identical to turbine pump 30 and thus includes a turbine impeller 51 supported upon an arbor 52. Turbine pump 50 further includes a generally cylindrical rotor 53 which is joined to the outer edges of turbine impeller 51 and is therefore rotatable therewith. A cylindrical isolator 55 is preferably formed of a suitable glass material and is fixed to the interior of pump receptacle 23 of housing 11. Isolator 55 is spaced from rotor 53 such that an air gap 54 is formed between rotor 53 and isolator 55. A motor core 56 encloses isolator 55 and is similarly fixed within pump receptacle 23. Turbine pump 50 further includes an outer core ring 57 encircling the outer surface of motor core 56. Turbine pump 50 further includes windings 60 and 61 on either side of outer core ring 57 which similarly encircle motor core 56.

Turbine pump 50 further includes a deswirler 62 having a deswirler body 63 which supports a plurality of curved deswirler vanes 64. Deswirler vanes 64 extend from deswirler body 63 and are fixed within the interior of pump receptacle 23 of housing 11 and secure the position of deswirler 62 therein. Deswirler body 63 further supports a bushing 65 which in turn receives the remaining end of arbor 52. A flared portion 67 is formed between the end of arbor 52 and the end of bushing 65 to provide a thrust load carrying surface which maintains arbor 52 within bushing 65. Arbor 52 is rotatable within bushing 65 such that a bearing is formed therebetween. In the preferred fabrication of the present invention, arbor 52 and bushing 65 are made of a jewel bearing material such as sapphire, or the like.

In operation, artificial heart 10 is positioned within a patient's circulatory system in the manner described in the above-referenced incorporated co-pending patent application utilizing suitable connecting apparatus (not shown) for securing input couplers 12 and 14 as well as output couplers 13 and 15 to the patient's blood vessels. As is also described in the above-referenced incorporated co-pending patent application, a power and control system (not shown) is operatively coupled to the electric motor windings within turbine pumps 30 and 50 to provide energizing and control signals for operation of the electric motors therein. As turbine impellers 31 and 51 are caused to rotate, a flow of blood is induced which flows into input passage 20 of input coupler 12 and thereafter through turbine impeller 31 and deswirler 42 through Venturi passage 24 and into pump receptacle 23. This flow continues and is increased by the rotation of turbine impeller 51. The resulting blood flow continues outwardly from pump receptacle 23 past deswirler 62 exiting through output passage 26 of output coupler 13. In accordance with an important aspect of the present invention, the blood flows induced by the rotations of turbine impellers 31 and 51 each immediately flow through the structures of deswirlers 42 and 62 respectively. It will be noted that deswirler vanes 44 of deswirler 42 are oppositely curved with respect to the vanes of turbine impeller 31. This relationship allows deswirler 42 to overcome or straighten the rotational vortex turbulence induced within the blood low as turbine impeller 31 is rotated. This operation is often referred to in the art as "flow straightening". As a result the blood flow leaving deswirler 42 and entering Venturi passage 24 is substantially free of rotational vortex turbulence. A similar oppositely curved relationship exists between deswirler vanes 64 and turbine impeller 51. Accordingly, deswirler 62 is similarly operative to ensure that the outward blood flow through output passage 21 of output coupler 15 is also substantially free of rotational vortex turbulence.

It has been determined that the size of gap 46 between turbine impeller 31 and deswirler 42 and the size of gap 66 between turbine impeller 51 and deswirler 62 are critical to the proper operation of flow straightening. Accordingly, gaps 46 and 66 are preferably maintained at 0.5 millimeters.

FIG. 5 sets forth a section view of artificial heart 10 taken along section lines 5-5 in FIG. 2. As described above artificial heart 10 includes a housing 11 supporting input coupler 14 and output coupler 15. Input coupler 14 further defines an input passage 27 extending through input coupler 14. Correspondingly, output coupler 15 defines an output passage 28 extending through output coupler 15. Housing 11 further defines a pump receptacle 122 within which a turbine pump 130 is supported. Housing 11 also further defines a pump receptacle 123 within which a turbine pump 150 is supported. Pump receptacles 122 and 123 are coupled by a Venturi passage 124 such that a continuous blood flow passage between input passage 27 of input coupler 14 and output passage 28 of output coupler 15 is formed. Also shown is crisscrossing Venturi passage 24. It should be noted that passages 124 and 24 are oval in cross section to reduce the overall height of artificial heart 10.

Turbine pump 130 includes a turbine impeller 131 supported upon an arbor 132. Turbine pump 130 further includes a generally cylindrical rotor 133 which is joined to the outer edges of turbine impeller 131 and is therefore rotatable therewith. A cylindrical isolator 135 is preferably formed of a suitable glass material and is fixed to the interior of pump receptacle 122 of housing 101. Isolator 135 is spaced from rotor 133 such that an air gap 134 is formed between rotor 133 and isolator 135. A motor core 136 encloses isolator 135 and is similarly fixed within pump receptacle 122. Turbine pump 130 further includes an outer core ring 137 encircling the outer surface of motor core 136. Turbine pump 130 further includes windings 140 and 141 on either side of outer core ring 137 which similarly encircle motor core 136.

Turbine pump 130 further includes a deswirler 142 having a deswirler body 143 which supports a plurality of curved deswirler vanes 144. Deswirler vanes 144 extend from deswirler body 143 and are fixed within the interior of Venturi passage 124 of housing 101 and secure the position of deswirler 142 therein. Deswirler body 143 further supports a bushing 145 which in turn receives the remaining end of arbor 132. A flared portion 147 is formed between the end of arbor 132 and the end of bushing 145 to provide a thrust load carrying surface which maintains arbor 132 within bushing 145. Arbor 132 is rotatable within bushing 145 such that a bearing is formed therebetween. In the preferred fabrication of the present invention, arbor 132 and bushing 145 are made of a jewel bearing material such as sapphire, or the like.

Turbine pump 150 is virtually identical to turbine pump 130 and thus includes a turbine impeller 151 supported upon an arbor 152. Turbine pump 150 further includes a generally cylindrical rotor 153 which is joined to the outer edges of turbine impeller 151 and is therefore rotatable therewith. A cylindrical isolator 155 is preferably formed of a suitable glass material and is fixed to the interior of pump receptacle 123 of housing 101. Isolator 155 is spaced from rotor 153 such that an air gap 154 is formed between rotor 153 and isolator 155. A motor core 156 encloses isolator 155 and is similarly fixed within pump receptacle 123. Turbine pump 150 further includes an outer core ring 157 encircling the outer surface of motor core 156. Turbine pump 150 further includes windings 160 and 161 on either side of outer core ring 157 which similarly encircle motor core 156.

Turbine pump 150 further includes a deswirler 162 having a deswirler body 163 which supports a plurality of curved deswirler vanes 164. Deswirler vanes 164 extend from deswirler body 163 and are fixed within the interior of pump receptacle 123 of housing 101 and secure the position of deswirler 162 therein. Deswirler body 163 further supports a bushing 165 which in turn receives the remaining end of arbor 152. A flared portion 167 is formed between the end of arbor 152 and the end of bushing 165 to provide a thrust load carrying surface which maintains arbor 152 within bushing 165. Arbor 152 is rotatable within bushing 165 such that a bearing is formed therebetween. In the preferred fabrication of the present invention, arbor 152 and bushing 165 are made of a jewel bearing material such as sapphire, or the like.

In operation, and as described above, artificial heart 10 is positioned within a patient's circulatory system in the manner described in the above-referenced incorporated co-pending patent application utilizing suitable connecting apparatus (not shown) for securing input couplers 12 and 14 as well as output couplers 13 and 15 to the patient's blood vessels. As is also described in the above-referenced incorporated co-pending patent application, a power and control system (not shown) is operatively coupled to the electric motor windings within turbine pumps 130 and 150 to provide energizing and control signals for operation of the electric motors therein. As turbine impellers 131 and 151 are caused to rotate, a flow of blood is induced which flows into input passage 27 of input coupler 14 and thereafter through turbine impeller 131 and deswirler 142 through Venturi passage 124 and into pump receptacle 123. This flow continues and is increased by the rotation of turbine impeller 151. The resulting blood flow continues outwardly from pump receptacle 123 past deswirler 62 exiting through output passage 28 of output coupler 15. In accordance with an important aspect of the present invention, the blood flows induced by the rotations of turbine impellers 131 and 151 each immediately flow through the structures of deswirlers 142 and 162 respectively. It will be noted that deswirler vanes 144 of deswirler 142 are oppositely curved with respect to the vanes of turbine impeller 131. This relationship allows deswirler 142 to overcome or straighten the rotational vortex turbulence induced within the blood low as turbine impeller 131 is rotated. This operation is often referred to in the art as "flow straightening". As a result the blood flow leaving deswirler 142 and entering Venturi passage 124 is substantially free of rotational vortex turbulence. A similar oppositely curved relationship exists between deswirler vanes 164 and turbine impeller 151. Accordingly, deswirler 162 is similarly operative to ensure that the outward blood flow through output passage 28 of output coupler 15 is also substantially free of rotational vortex turbulence.

It has been determined that the size of gap 146 between turbine impeller 131 and deswirler 142 and the size of gap 166 between turbine impeller 151 and deswirler 162 are critical to the proper operation of flow straightening. Accordingly, gaps 146 and 166 are preferably maintained at 0.5 millimeters.

What has been shown is an artificial heart which provides an implantable housing supporting a redundant set of series coupled servo driven turbine impeller pump portions to provide blood circulation within a host patient. Each turbine impeller pump utilizes a deswirler which cooperates with the turbine pump to augment the blood flow pattern produced by the rotating action of the turbine pump thereby producing a substantially turbulence free blood flow.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

That which is claimed is:

1. An artificial heart comprising:
   a housing having a common surface, a first input connector upon said common surface, a first input turbine receptacle, a first output turbine receptacle, a first output connector upon said common surface, and a first U-shaped coupling passage between said first input turbine receptacle and said first output turbine receptacle, said housing further having a second input connector upon said common surface, a second input turbine receptacle, a second output turbine receptacle, a second output connector upon said common surface, and a second U-shaped coupling passage between said second input turbine receptacle and said second output turbine receptacle;
   a first turbine pump having a first deswirler and defining a first turbine axis, supported within said first input turbine receptacle, said first turbine pump operative to flow blood from said first input connector through said first U-shaped coupling passage and through said first output connector;
   a second turbine pump having a second deswirler and defining a second turbine axis, supported within said second output turbine receptacle said second turbine pump operative to flow blood from said first input connector through said first U-shaped coupling passage and through said first output connector;
   a third turbine pump having a third deswirler and defining a third turbine axis, supported within said second input turbine receptacle, said third turbine pump operative to flow blood from said second input connector through said second U-shaped coupling passage and through said second output connector; and
   a fourth turbine pump having a fourth deswirler and defining a fourth turbine axis, supported within said second output turbine receptacle, said fourth turbine pump operative to flow blood from said second input connector through said second U-shaped coupling passage and through said second output connector.

2. An artificial heart comprising:
   a housing having a common surface, first and second input connectors extending from said common connector surface, first and second input turbine receptacles, first and second output turbine receptacles, first and second output connectors extending from said common surface, and a first U-shaped coupling passage between said first input turbine receptacle and said first output turbine receptacle, said housing further having a second U-shaped coupling passage between said second input turbine receptacle and said second output turbine receptacle;
   a first turbine pump having a first deswirler and defining a first turbine axis, supported within said first input turbine receptacle, said first turbine pump operative to flow blood from said first input connector through said first U-shaped coupling passage and through said first output connector;
   a second turbine pump having a second deswirler and defining a second turbine axis, supported within said second output turbine receptacle said second turbine pump operative to flow blood from said first input connector through said first U-shaped coupling passage and through said first output connector;
   a third turbine pump having a third deswirler and defining a third turbine axis, supported within said second input turbine receptacle, said third turbine pump operative to flow blood from said second input connector through said second U-shaped coupling passage and through said second output connector; and
   a fourth turbine pump having a fourth deswirler and defining a fourth turbine axis, supported within said second output turbine receptacle, said fourth turbine pump operative to flow blood from said second input connector through said U-shaped second coupling passage and through said second output connector.

* * * * *